(12) United States Patent
McVey et al.

(10) Patent No.: US 7,361,304 B2
(45) Date of Patent: Apr. 22, 2008

(54) BUILDING DECONTAMINATION WITH VAPOROUS HYDROGEN PEROXIDE

(75) Inventors: Ian F. McVey, Lakewood, OH (US); Victor M. Selig, Euclid, OH (US); Lewis I. Schwartz, Shaker Heights, OH (US); Gerald E. McDonnell, Basingstoke (GB); Peter A. Burke, Concord, OH (US)

(73) Assignee: Steris Inc., Temecula, CA (US)

( * ) Notice: Subject to any disclaimer, the term of this patent is extended or adjusted under 35 U.S.C. 154(b) by 595 days.

(21) Appl. No.: 10/767,908

(22) Filed: Jan. 29, 2004

(65) Prior Publication Data

US 2004/0184950 A1  Sep. 23, 2004

Related U.S. Application Data

(60) Provisional application No. 60/444,073, filed on Jan. 31, 2003.

(51) Int. Cl.
*A61L 2/20* (2006.01)

(52) U.S. Cl. ........................ 422/28; 422/123; 588/299; 588/300; 588/313

(58) Field of Classification Search ............... 422/4, 422/123, 305, 306, 28; 588/299, 300, 313
See application file for complete search history.

(56) References Cited

U.S. PATENT DOCUMENTS

| | | | |
|---|---|---|---|
| 4,169,123 A | 9/1979 | Moore et al. | |
| 4,909,999 A | 3/1990 | Cummings et al. | |
| 5,068,087 A | 11/1991 | Childers | |
| 5,173,258 A | 12/1992 | Childers | |
| 5,258,162 A | 11/1993 | Andersson et al. | |
| 5,282,770 A | 2/1994 | Shibata ........................ 454/239 |
| 5,779,973 A | 7/1998 | Edwards et al. | |
| 5,788,925 A | 8/1998 | Pai et al. | |
| 5,792,435 A | 8/1998 | Mueller et al. | |
| 6,293,861 B1 | 9/2001 | Berry ........................ 454/255 |
| 6,583,726 B1 | 6/2003 | Johnson et al. ............. 340/627 |
| 6,656,434 B1 | 12/2003 | DeMarcki .................... 422/120 |
| 2002/0114727 A1* | 8/2002 | McVey et al. .................. 422/4 |
| 2003/0035754 A1* | 2/2003 | Sias et al. ..................... 422/29 |
| 2003/0143108 A1 | 7/2003 | Wasinger ..................... 422/28 |
| 2003/0171092 A1* | 9/2003 | Karamanos et al. ........ 454/233 |
| 2004/0005240 A1* | 1/2004 | Adiga et al. .................... 422/1 |
| 2004/0084899 A1* | 5/2004 | Gonzales et al. ........... 285/179 |
| 2005/0084415 A1* | 4/2005 | McVey et al. ................ 422/28 |

FOREIGN PATENT DOCUMENTS

DE  2060895  6/1972

(Continued)

*Primary Examiner*—Gladys J P Corcoran
*Assistant Examiner*—Sean E. Conley
(74) *Attorney, Agent, or Firm*—Fay Sharpe LLP

(57) ABSTRACT

When microbial contamination is introduced into a room (20*) of an enclosure, such as a building, an HVAC system including supply ductwork (16) and a return ductwork (34) is decontaminated with hydrogen peroxide vapor. A decontamination controller (46) operates controllable baffles (22) at outlet registers (20), temporary controllable baffles (44) at inlet registers (30), and a blower system (10) to circulate hydrogen peroxide vapor from hydrogen peroxide vapor generators (42) through the ductwork in both forward and reverse directions. Further, at least portions of the baffles are closed to create dwell times in which the hydrogen peroxide vapor resides in the ductwork with minimal or turbulent flow.

18 Claims, 1 Drawing Sheet

FOREIGN PATENT DOCUMENTS

| | | |
|---|---|---|
| EP | 431 648 A1 | 6/1991 |
| GB | 792033 | 3/1958 |
| WO | WO 02/07860 A2 | 1/2002 |
| WO | WO 02/066082 | 8/2002 |
| WO | WO 03/035118 | 5/2003 |
| WO | WO 03/090875 | 11/2003 |

* cited by examiner

BUILDING DECONTAMINATION WITH VAPOROUS HYDROGEN PEROXIDE

This application claims the benefit of U.S. Provisional Application Ser. No. 60/444,073, filed on Jan. 31, 2003, which is incorporated herein in its entirety, by reference.

BACKGROUND OF THE INVENTION

The present invention relates to the microbial decontamination arts. It finds particular application in conjunction with sporicidal decontamination of heating, ventilation, and cooling (HVAC) systems and will be described with particular reference thereto. However, it is to be appreciated that the present invention is also applicable to other types of microorganisms and to other decontamination applications.

HVAC systems typically include a series of delivery ducts, which deliver heated or cooled air from one or more heat exchangers to individual rooms or offices. The duct is typically largest in cross section adjacent the heat exchanger and diminishes in cross section as it branches to supply treated air to the individual rooms and offices. Typically, baffles at the register outlets and, in some systems, at various points along the ductwork system, control the relative amounts of air delivered to each room or register outlet. In modern construction, the baffles are sometimes motorized in order to provide individual room temperature control. The automated baffles are also used for safety, such as to shut down the supply of air if a fire is detected.

HVAC systems typically include a return system for returning air from the rooms to the heat exchanger. Some systems use a central return, which delivers return air from a central location to the heat exchanger to be retreated and recirculated. Other systems include a plenum, often defined by the open space above acoustic ceiling tiles, through which air is drawn back to the heat exchanger. Often, the plenums interconnect with ductwork, which conveys the return air back to the heat exchanger. Other systems include ductwork extending from a return register in each room. These individual ducts merge into progressively larger ducts as they approach the heat exchanger.

Blower motors and filters located adjacent the heat exchanger propel the treated air through the delivery duct system to the individual rooms and draw return air back to and through the heat exchanger. The ducts themselves are typically galvanized steel or aluminum. Portions of the ductwork or plenum may include acoustic material. In older buildings, the ductwork may have an accumulated layer of dust, dirt, and grease.

Large enclosures, such as rooms and buildings tend to become contaminated with a wide variety of microbial contaminants, including bacteria, molds, fungi, yeasts, and the like. These microorganisms thrive in damp spaces, such as behind walls, in plaster, under counters in bathroooms, and in ductwork and tend to be very difficult to eradicate. Some contaminants are brought into the room in the air, both through doorways, windows and the like as well as through ventilation systems. Contaminants are also carried into the room on the clothing or person by people using the room and from breathing. Some microbes cause a musty smell. Others can infect later users of the room. Additionally, there is a possibility that a room may be intentionally contaminated with pathogenic microorganisms, such as anthrax spores, smallpox virus, or the like. Some contaminants, such as tobacco smoke, body perfume, and medicinal odors are non-microbial.

When microbial contamination is introduced into a building, such as an Anthrax spore laced letter, the microbes tend to become airborne and are drawn into and pumped through the HVAC system. Killing spores and other microbes in the relatively inaccessible ductwork of the HVAC system has proven difficult.

The present invention provides a new and improved decontamination system and method which overcome the above-referenced problems, and others.

SUMMARY OF THE INVENTION

In accordance with one aspect of the present invention, a building decontamination system is provided. The system includes a means for circulating air through a ductwork system and a means for supplying a decontamination vapor to the ductwork system to be circulated through it.

In accordance with another aspect of the present invention, a method of decontaminating buildings is provided. A vapor decontaminant is circulated through an HVAC ductwork system and associated rooms of the building.

One advantage of the present invention resides in its efficacy in microbially decontaminating ductwork.

Another advantage of the present invention resides in its efficacy of decontaminating buildings.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts. The drawings are only for purposes of illustrating a preferred embodiment and are not to be construed as limiting the invention.

DETAILED DESCRIPTION OF THE PREFERRED EMBODIMENTS

Figure 1:
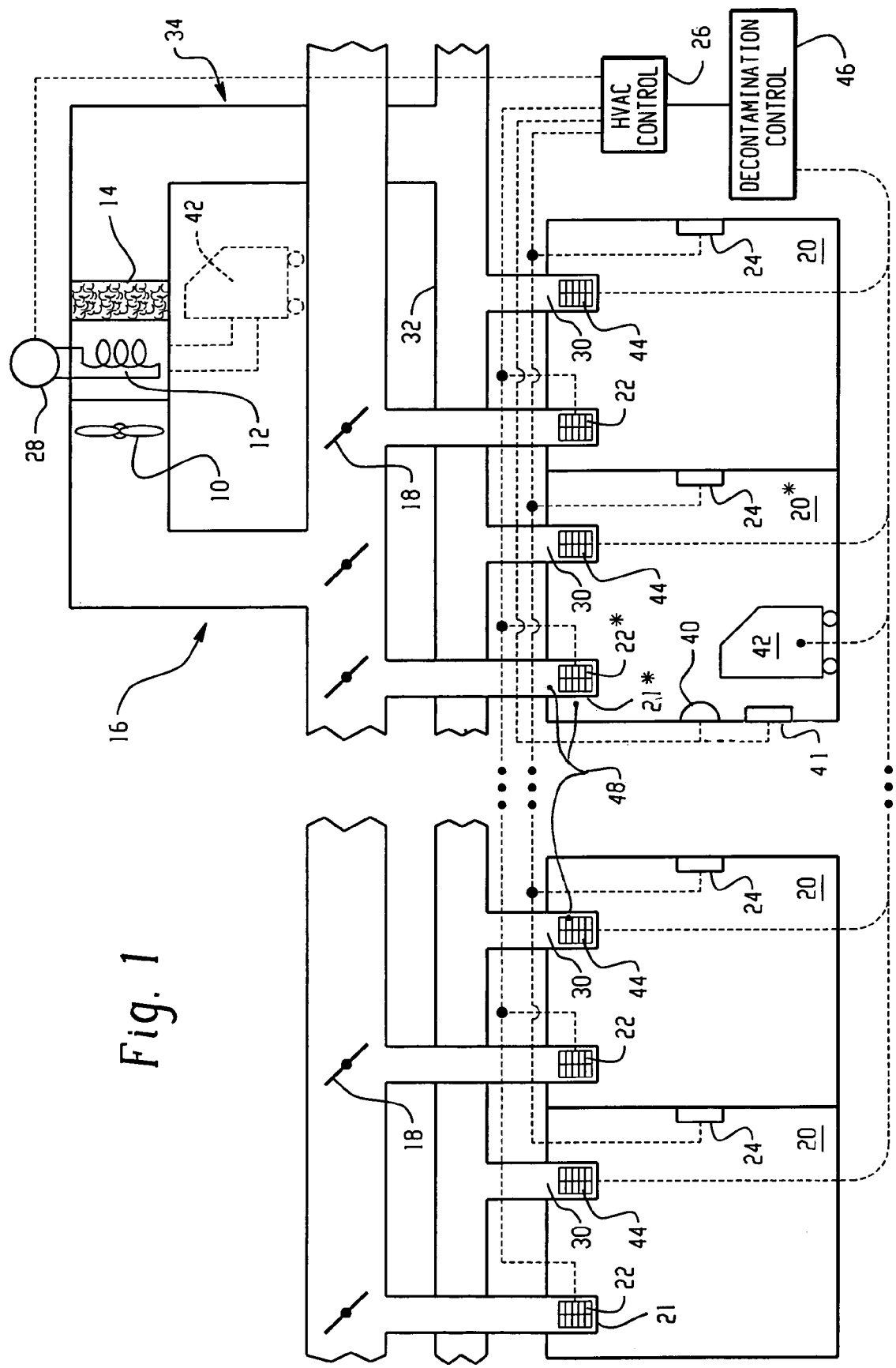
FIG. 1 is a diagrammatic illustration of an HVAC system in combination with a vapor hydrogen peroxide decontamination system.

Commercial buildings and other large enclosures typically include several heat exchanger and delivery and return ductwork subsystems or zones, each heating or cooling a distinct area of the building. In each of a plurality of heating and cooling zones of a large building, a fan or blower 10 draws air through a heat exchanger 12 and a filter 14. The fan propels heated air (in the winter) or cooled air (in the summer) through a delivery duct system 16. The delivery duct system includes branches, turns, and various angles. Adjustable baffles 18 are located at various points within the delivery duct system to control the relative airflow to the various branches.

The delivery duct system delivers heated or cooled air to each of a plurality of regions, such as offices or other rooms 20. At each room or office, a heat delivery register 21 with a control valve or baffle 22 is connected with the delivery duct system. Preferably, each room or office further includes a thermostat 24. In a preferred modern office environment, the thermostats 24 are connected with a central electronic control 26, which controls the corresponding register valve or baffle 22 to regulate temperature within each room or office. The controller further controls a source 28 of heated or cooled liquid to the heat exchanger, such as cooling tower, to be sure that an adequate supply of heating or cooling is delivered to maintain all of the rooms or offices at the selected temperatures. In older buildings, the baffle 22 at the registers 21 is manually adjustable.

On a return side, each room or office includes a return register 30 that interconnects with one or more common plenums 32, such as an air space above the acoustic ceiling of several offices. The plenum is connected with a return duct system 34 through which air is drawn from the plenum back to the filter 14 and heat exchanger 12. Alternately, the return registers can be connected directly to the return ducts.

When contamination is introduced into the building, it may be done by opening a letter or package in one of the offices 20☆. If doors to the office are open, some of the airborne spores will be carried into an adjacent hallway and other offices. Many of the spores will be drawn through the return register 30☆ into the plenum 32 where some of the spores or other microbes will be deposited on plenum surfaces. Most of the spores will be drawn into the return duct 34 where many will again be deposited on return duct surfaces. Because the filter 14 is typically a dust filter and not a HEPA filter, the filter typically traps some of the spores, but permits many others to pass into the heat exchanger 12 and into the delivery duct system 16. Moreover, some of the spores will pass down the hallway into adjoining HVAC subsystems and be pulled into other return and delivery duct systems.

First, to minimize the spread of the microbial decontamination, those offices or rooms in which mail will be opened are equipped with a panic switch 40 that is interconnected with the controller 26 for immediately stopping the circulation of air through the HVAC system. Where the baffles 22 are controllable, the HVAC system also immediately closes all baffles.

Alternatively or additionally, one or more automated detectors 41 for one or more hazardous airborne materials are located in the mail handling room. The detector(s) are interconnected with the controller for immediately stopping the circulation of air through the HVAC system. An associated alarm system is activated by the controller in the event that hazardous material is detected.

Once all personnel have been evacuated and decontaminated as necessary, the source of the microbial contamination is removed or destroyed.

Next, the office or offices that were directly contacted by the source of contamination are decontaminated with a gaseous decontaminant, preferably hydrogen peroxide vapor. More specifically to the first embodiment, a hydrogen peroxide vapor generator 42 is wheeled into or connected with the contaminated room or office 20☆. The inlet register 21☆ is sealed and the return register 30☆ is sealed. When automated baffles are available, the automated baffles can be used to seal the registers. Alternately, the registers are covered, such as with plastic or metal foil. The covering can be held in place with tape, magnets, or the like. The vapor hydrogen peroxide generator 42 fills the room or office 20☆ with hydrogen peroxide vapor which is held in the room with an appropriate concentration and for an appropriate time to kill the microbial contamination at issue. A decontamination control system 46 controls the supply of vapor to the room 20☆.

Next, or before decontaminating the most contaminated room, the building is cordoned off or partitioned in accordance with HVAC subsystems or zones. In general, any of the HVAC subsystems might be contaminated with the microbes. The microbes may have been circulated through the air, particularly if the HVAC systems were not shut off promptly. Further, microbes may have been carried from zone to zone by personnel evacuating the facility. The HVAC subsystems can be decontaminated one by one, or concurrently by a plurality of decontamination teams. Preferably, the decontamination process is started at the HVAC subsystems that are most remote from the contamination site 20☆.

To decontaminate each HVAC subsystem, vapor hydrogen peroxide is circulated through each HVAC subsystem. It will be noted that with a steady-state flow, certain areas of the ductwork will be shielded from flowing hydrogen peroxide vapor. For example, turbulent flow at square corners will tend to leave an untreated or cold spot just past the corner. Similarly, ridges in the ductwork, baffles, and the like will have untreated or cold spots on their downstream or leeward sides. To be sure that all of these areas are treated, once the ductwork is filled with vapor hydrogen peroxide and plain air is flushed out, the airflow is stopped and permitted to dwell in the ductwork system for a preselected duration. Then, circulation is recommenced. Preferably, each time circulation is recommenced, the flow direction through the ductwork is reversed. The reversed flow preferably continues until the partially spent vapor hydrogen peroxide that had dwelled in the ductwork system is flushed out and replaced by new vapor hydrogen peroxide. Circulation is again stopped for another dwell period. The number of times that this fill, dwell, and flush cycle is repeated will vary with the type of decontamination and the ductwork system. For example, ductwork with an accumulation of dust and dirt may be more difficult to decontaminate than a ductwork system that has a clean, smooth metallic surface.

The entire HVAC subsystem need not be subject to the fill, dwell, and flush stages concurrently. Rather, in another embodiment, once the ductwork is filled, a first fraction of the inlet and outlet registers is closed to create a dwell phase while the vapor hydrogen peroxide continues to circulate through other parts of the same HVAC subsystem. After the first portion of the HVAC system has undergone the dwell phase, those registers can be opened for a flush a refill phase while another group of registers are closed to bring that section of the ductwork into the dwell phase. In this manner, the open and closed registers are cycled such that all duct areas receive a combination of flowing and static vapor.

One or more of temperature, vapor concentration, and flow rate monitors 48 in the incoming and/or return ductwork or room optionally measure properties of the vapor, allowing the decontamination control system 46 to adjust decontamination parameters such as vapor concentration, flow rates, room temperatures, decontamination time, and the like to ensure decontamination.

Preferably, the anti-microbial vapor is introduced in the rooms or offices for circulation. This can be achieved by placing a vapor hydrogen peroxide generator in each room or by connecting a larger generator to a plurality of rooms with temporary, portable ducts. In an alternate embodiment, the hydrogen peroxide generator is tapped into the heat exchanger. This can be done by cutting through the side wall of the heat exchanger or associated ductwork, by interconnecting through the openings for changing filters, through access panels, or the like. When the vapor is introduced at a central location, like the heat exchanger, a supplemental blower associated with the generator can blow the vapor into both the feed and return ducts, concurrently.

In another embodiment, the airflow through the ductwork is pulsed. That is, ductwork is designed for smooth, laminar flow. The circulation of the air is pulsed into high and low or no velocity periods to create turbulence to bring the vapor into contact with all surface portions.

To facilitate remote, automated control, a temporary baffle is in the form of a balloon is inserted in the input registers without remote controlled baffles and into return registers. The balloon is inflated to block or substantially block the outlet during the pause portions and is deflated to permit fluid flow during the forward and reverse flow portions of the cycle. The balloons can be controlled pneumatically or an associated electric pump can be controlled electrically.

In another embodiment, electrically operated baffles 44 are installed temporarily over registers 21 and/or registers 30 that do not have controllable baffles. The electrically operated baffles are plugged into a convenient electrical outlet in the room to provide a source of electricity. Each baffle preferably includes a radio receiver for receiving open and close commands. Baffles that leak slightly are advantageous for preventing dead legs in the ductwork which are difficult to fill with the vapor. More preferably, each of the remotely operable baffles is operable by the decontamination control system 46. The decontamination control system 46 is also connected with the monitors and the blower for circulating air through the ductwork for automatically controlling a decontamination cycle.

Further, concentration monitors 48 are preferably incorporated at each temporary baffle to provide the decontamination control system 46 with immediate feedback of vapor concentrations at the various registers. Additional concentration sensors 48 are preferably mounted in the individual offices, at the heat exchanger, and at other accessible locations in the ductwork. The sensors detect the concentration of hydrogen peroxide and/or water vapor in the room and ductwork. The sensors are connected with the decontamination control system 46. The control system responds to the detected concentrations of water vapor and/or hydrogen peroxide by adjusting one or more of hydrogen peroxide concentration in the vapor, flow rates, exposure times, and the like to maintain suitable conditions for decontamination. For example, the decontamination control system 46 dynamically adjusts the decontamination cycles to maintain preselected minimum hydrogen peroxide concentrations at all locations. The decontamination control system 46 further controls the vapor hydrogen peroxide generator(s) 42 to increase or decrease vapor production rates, as may be necessary, to maintain the preselected concentrations. The decontamination control system 46 optionally models the duct system in order to determine optimal supply and flow rates, cycle timing, and the like. In this manner, the decontamination controller 46 takes into account long runs, unbalanced branching of the supply and return ducts, potential cold spots in the ductwork, and other problematic locations. The control system may include a processor which is preprogrammed to optimize and implement a decontamination cycle which includes flowing vapor through the duct system in one direction, allowing the vapor to stagnate in the system, and flowing the vapor in an opposite direction.

When the ductwork is configured such that additional hydrogen peroxide needs to be added at various locations around the ductwork, flexible hoses are connected with the vapor hydrogen peroxide generator and threaded through the ducts to such locations. Preferably, the above-described vapor cycles are performed first. If there is any dirt, dust, or loose materials in the ductwork, threading hoses through the duct system could dislodge them, allowing them to fall, cover, and shield spores or other microbes. The hose, particularly a porous hose, delivers high concentrations of the vapor directly to problem areas of the duct. In one embodiment, the hose has high velocity nozzles such that the vapor is ejected at high velocities deliberately disturbing and suspending dirt and dust that may be lining the walls of the ductwork. The blower circulates the disturbed and suspended dust and dirt particles to HEPA filters located at the heat exchanger and at each register. The individual HEPA are removed and subject to a heavy-duty decontamination process, such as immersion in a liquid decontaminant, incineration, or the like. The flexible hose or other flexible device may also be used to carry baffles into the ductwork to redirect vapor to portions of the ductwork with low flow rates and low vapor concentrations. The flexible hose can also carry flow monitors to various points in the ductwork. Flow velocity, temperature, and other monitors, computer modeling, and the like are all used to optimize the decontamination process. The flexible elements can also carry contamination detectors, biological sampling devices, and the like.

Further, spore strips 60 can be positioned at the registers in the heat exchanger, or at various locations in the ductwork prior to treatment. After the treatment has been completed, the spore strips are incubated to assure successful decontamination.

The system is suited to decontamination of a wide variety of buildings, including offices, research facilities, factories, schools, hospitals, and hotels. Portions of buildings having individual ductwork systems can also be treated, such as hotel suites having a bathroom in addition to one or more bedroom areas. Passenger vehicles having ductwork, such as ships, airplanes, and the like may also be decontaminated.

Different levels of decontamination are contemplated. As used herein, the term "decontamination," and its equivalents, is intended to encompass both microbial decontamination as well as chemical decontamination—the destruction of chemical agents, or their conversion to harmless or odorless compounds. Decontamination also encompasses the neutralizing of unpleasant odors, such as tobacco smoke, perfume, or body odor residues, and odors and dampness due to molds. "Microbial decontamination" is used herein to encompass the destruction of biological contaminants, specifically, living microorganisms, and also the destruction or inactivation of pathogenic forms of proteinaceous-infectious agents (prions). The term microbial decontamination encompasses sterilization, the highest level of biological contamination control, which connotes the destruction of all living microorganisms. The term also includes disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which are destroyed in the decontamination process include bacterial spores, vegetative bacteria, viruses, molds, and fungi. Some of these are capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli*, Salmonella), and the like.

Exemplary pathogenic chemical agents include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N, N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

Hydrogen peroxide vapor is a particularly effective microbial and chemical decontaminant because it has broad spectrum activity against a wide variety of pathogenic microorganisms and chemical pathogenic agents, such as hard to destroy spores of *Bacillus stearothermophilus, Bacillus anthracis*, smallpox virus, and the like. It is also effective at or close to room temperature (e.g., 15-30° C.), making it suitable for decontamination of enclosures with little or no heating. Hydrogen peroxide vapor has a good material compatibility, rendering it safe for use with a variety of equipment and materials, including electronic equipment, soft furnishings, brass and chrome fixtures, and the like. It also degrades to water and oxygen over time, which are not harmful to people subsequently entering the treated space. Where low levels of hydrogen peroxide (about 1 ppm, or less) remain in the room after decontamination, this is not considered to pose a risk to the occupants.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of decontaminating buildings comprising:
   determining the location of a contamination site within a building;
   dividing HVAC ductwork in said building into a plurality of independent HVAC ductwork subsystems;
   circulating a vapor decontaminant through the HVAC ductwork and associated rooms such that decontamination of the HVAC subsystems occurs in more remote locations from the contamination site within the building first, and then progressively decontaminating the HVAC subsystems closer to the contamination site.

2. The method as set forth in claim 1 wherein the vapor decontaminant includes hydrogen peroxide vapor.

3. The method as set forth in claim 2, wherein the ductwork includes a plurality of ducts and the circulating step includes:
   circulating the hydrogen peroxide vapor alternately in the one direction and the opposite direction in each duct of the plurality of the ducts.

4. The method as set forth in claim 1, further including:
   automatically adjusting baffles located at least one of within the ductwork and at registers of the ductwork remotely to control the circulating of the decontaminant vapor.

5. The method as set forth in claim 1, further including:
   circulating the vapor contaminant alternately in one direction and then in an opposite direction through the HVAC subsystems ductwork.

6. The method as set forth in claim 1, further including:
   controlling the circulating of the vapor decontaminant to create turbulent flow in the ductwork.

7. The method as set forth in claim 1, further including:
   stopping the circulating of the vapor decontaminant through the HVAC subsystems ductwork and allowing the vapor to dwell in the ductwork;
   recommencing circulation of the vapor decontaminant.

8. The method as set forth in claim 7, wherein the vapor decontaminant is circulated in one direction prior to dwelling in the ductwork and circulated in an opposite direction after dwelling in the ductwork.

9. A method of decontaminating buildings comprising:
   circulating hydrogen peroxide vapor through HVAC ductwork and associated rooms, the circulating including:
      circulating the hydrogen peroxide vapor through the ductwork in one direction,
      circulating the hydrogen peroxide vapor through the ductwork in an opposite direction,
      alternately circulating the hydrogen peroxide vapor in the one direction and then the opposite direction through the ductwork, and
      allowing the hydrogen peroxide vapor to dwell in the ductwork.

10. The method as set forth in claim 9 further including:
    automatically opening and closing baffles at registers between the HVAC ductwork and individual rooms.

11. The method as set forth in claim 10 further including:
    monitoring at least one of temperature, flow velocity, and vapor concentration; and
    controlling the opening and closing of the baffles in accordance with the monitoring.

12. The method as set forth in claim 9 further including:
    creating turbulent flow in the ductwork.

13. A method of decontaminating a contaminated building comprising:
    installing a plurality of temporary baffles within the ductwork of the building to divide the ductwork into a plurality of HVAC subsystems, some of the subsystems being closer to a decontamination site than other HVAC subsystems;
    circulating a vapor decontaminant through HVAC ductwork and associated rooms;
    controlling the baffles to control a flow of vapor decontaminant through the HVAC subsystems and associated rooms to decontaminate the HVAC systems and associated rooms which are more remote from the contamination site first, and then progressively decontaminating HVAC subsystems and their associated rooms which are closer to the contamination site.

14. The method as set forth in claim 13, further including:
after decontaminating the HVAC ductwork and the associated rooms, removing the baffles and using the HVAC ductwork to heat/cool the associated rooms.

15. The method as set forth in claim 14, further including:
intermittently ceasing circulation of the vapor decontaminant through the HVAC ductwork, permitting the vapor decontaminant to dwell in the HVAC ductwork, and then recommencing circulation of the vapor decontaminant through the HVAC ductwork.

16. A method of decontaminating a contaminated building comprising:
connecting a temporary baffle with HVAC ductwork of the contaminated building;
alternating circulating the vapor decontaminant in one direction through the HVAC ductwork and then in an opposite direction through the HVAC ductwork;
controlling the temporary baffle to control a flow of vapor decontaminant from the HVAC ductwork to at least one of rooms and regions of rooms associated with the HVAC ductwork.

17. The method as set forth in claim 16, wherein the temporary baffle is controlled remotely.

18. The method as set forth in claim 16, wherein the temporary baffle is mounted within the ductwork.

* * * * *

UNITED STATES PATENT AND TRADEMARK OFFICE
CERTIFICATE OF CORRECTION

| | | |
|---|---|---|
| PATENT NO. | : 7,361,304 B2 | Page 1 of 1 |
| APPLICATION NO. | : 10/767908 | |
| DATED | : April 22, 2008 | |
| INVENTOR(S) | : McVey et al. | |

It is certified that error appears in the above-identified patent and that said Letters Patent is hereby corrected as shown below:

On the title page, item (75) Inventors, line 1, replace "Ian F. McVey" with "Iain McVey."

Signed and Sealed this
Eleventh Day of December, 2012

David J. Kappos
*Director of the United States Patent and Trademark Office*